(12) United States Patent
Boden et al.

(10) Patent No.: US 7,514,521 B2
(45) Date of Patent: Apr. 7, 2009

(54) METHOD FOR PREPARING A DIALKYL CARBONATE, AND ITS USE IN THE PREPARATION OF DIARYL CARBONATES AND POLYCARBONATES

(75) Inventors: Eugene Pauling Boden, Scotia, NY (US); Ganesh Kailasam, Murcia (ES); Larry Neil Lewis, Scotia, NY (US); Ignacio Vic Fernandez, Madrid (ES)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 1667 days.

(21) Appl. No.: 09/682,285

(22) Filed: Aug. 14, 2001

(65) Prior Publication Data

US 2003/0092872 A1  May 15, 2003

(51) Int. Cl.
*C08G 64/00* (2006.01)
*C08G 63/02* (2006.01)

(52) U.S. Cl. .................. 528/196; 422/130; 422/191; 528/198; 528/271; 528/272; 558/277

(58) Field of Classification Search .................. 422/130, 422/191; 528/196, 198, 271, 272; 558/277
See application file for complete search history.

(56) References Cited

U.S. PATENT DOCUMENTS

| | | | |
|---|---|---|---|
| 2,517,965 | A | 8/1950 | Bohl |
| 3,153,008 | A | 10/1964 | Fox |
| 4,182,726 | A | 1/1980 | Illuminati et al. |
| 4,218,391 | A | 8/1980 | Romano et al. |
| 4,318,862 | A | 3/1982 | Romano et al. |
| 4,360,659 | A | 11/1982 | Sikdar |
| 5,210,269 | A | 5/1993 | Di Muzio et al. |
| 5,527,943 | A | 6/1996 | Rivetti et al. |
| 5,536,864 | A | 7/1996 | Paret et al. |
| 5,599,965 | A | 2/1997 | Kricsfalussy et al. |
| 5,685,957 | A | 11/1997 | Rivetti et al. |
| 5,686,644 | A | 11/1997 | Rivetti et al. |
| 5,780,663 | A | 7/1998 | Mori et al. |
| 5,869,729 | A | 2/1999 | Nishihira et al. |

FOREIGN PATENT DOCUMENTS

| | | |
|---|---|---|
| EP | 0 634 390 | 12/1994 |
| JP | 1994092905 A | 4/1994 |
| WO | WO 03/016256 | 2/2003 |

OTHER PUBLICATIONS

Mauri, et al. "Dimethyl carbonate: a new building block for organic chemicals production". Ing. Chim. Ital., V. 21, N. 1-3, GEN- Mar. 1985 pp. 6-12.
Cassar, "Dimethylcarbonate: a new intermediate for a cleaner future*", Relazione presentata al Congresso Interdivisionale della Societa Chimica Italiana "CISCI '89" Perugia. Oct. 7-11, 1989. La Chimica & L'Industria. Doc. 43. pp. 18-22.
"GE licenses Enimont polycarb know-how", European Chemical News. Nov. 13, 1989. pp. 44.
"Enichem Licenses Its DMC, DPC Route". Chemical Marketing Reporter. vol. 236. No. 23. Dec. 4, 1989. pp. 29.
"EniMont-Lizenz an GE Plastics". Europa Chemie n 35/36 p. 585. Dec. 20, 1989 (Translation Attached) Total of 3 pgs.
U.S. Appl. No. 09/682,284, filed Aug. 14, 2001, Boden et al.
U.S. Appl. No. 09/682,286, filed Aug. 14, 2001, Boden et al.
U.S. Appl. No. 10/227,111, filed Aug. 23, 2002, Boden et al.
U.S. Appl. No. 10/250,067, filed Jun. 2, 2003, Boden et al.
Letter to Cantor Colburn, LLP from Richard L. Treanor at Oblon Spivak McClelland, Maier and Neustadt. Jul. 20, 2004. (2 pages).
M. M. Mauri, U. Romano, and F. Rivetti, Quad. Ing. Chim. Ital. (1985), vol. 21, No. 1-3, pp. 6-12.
(anonymous) "GE licenses Enimont polycarb know-how", European Chemical News, Nov. 13, 1989, p. 44.
L. Cassar, Chim. Ind. (Milan) (1990), vol. 72, No. 1, pp. 18-22.
International Search Report Dated Nov. 11, 2002.
Translation of excerpts of Building Permit for a new DMC Plant obtained by Polimeri Europa from the Ravenna, Italy local authority on May 22, 2001.

*Primary Examiner*—Terressa M Boykin

(57) ABSTRACT

Unexpected corrosion of downstream sections of a dialkyl carbonate manufacturing apparatus has been traced to alkyl chloroformate impurities, which slowly decompose to yield hydrochloric acid. An improved process and apparatus for dialkyl carbonate synthesis reduce corrosion by physically removing or chemically decomposing the alkyl chloroformate impurities within the corrosion-resistant upstream sections of the apparatus.

28 Claims, 7 Drawing Sheets

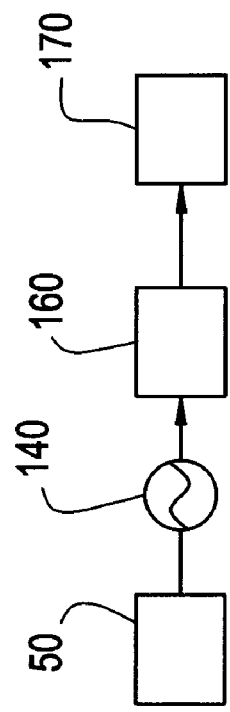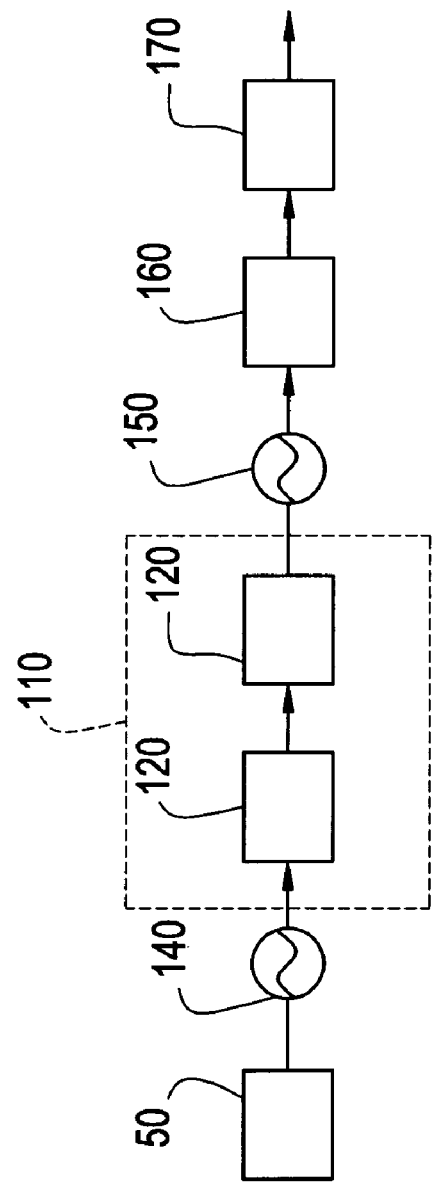

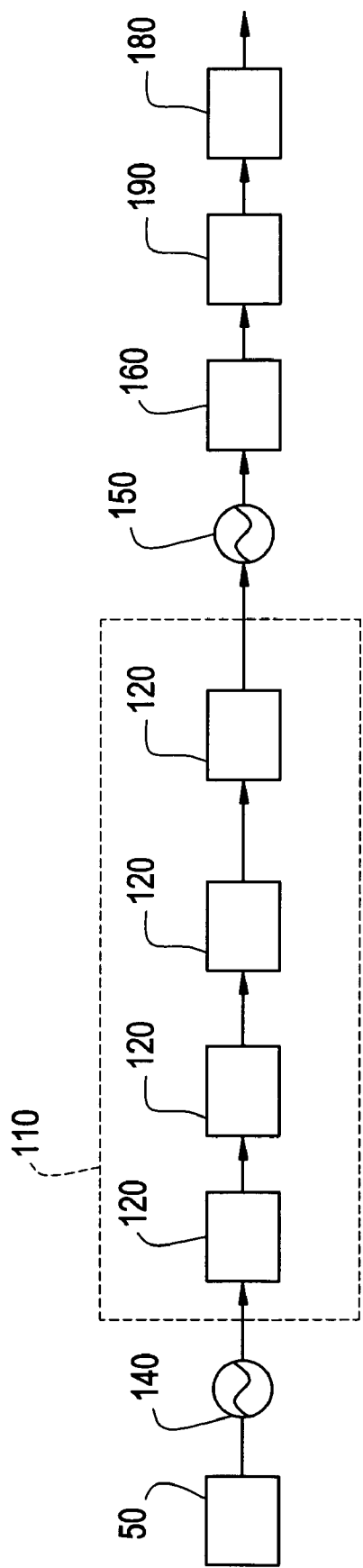
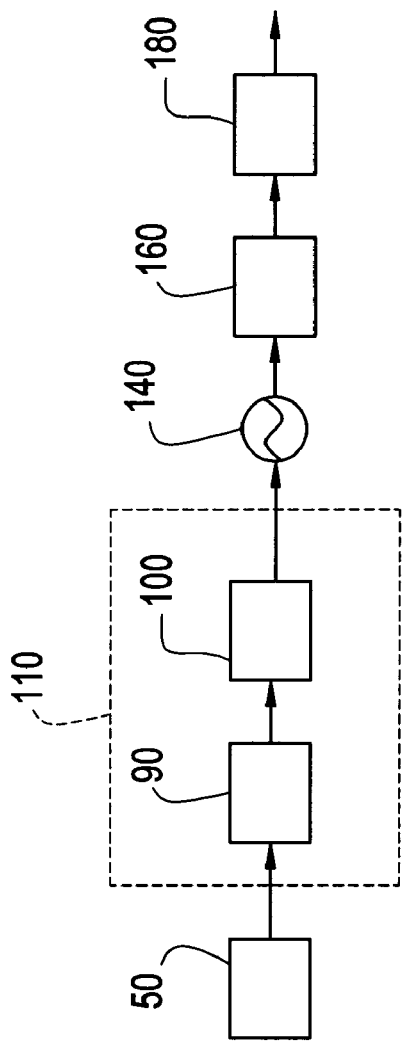

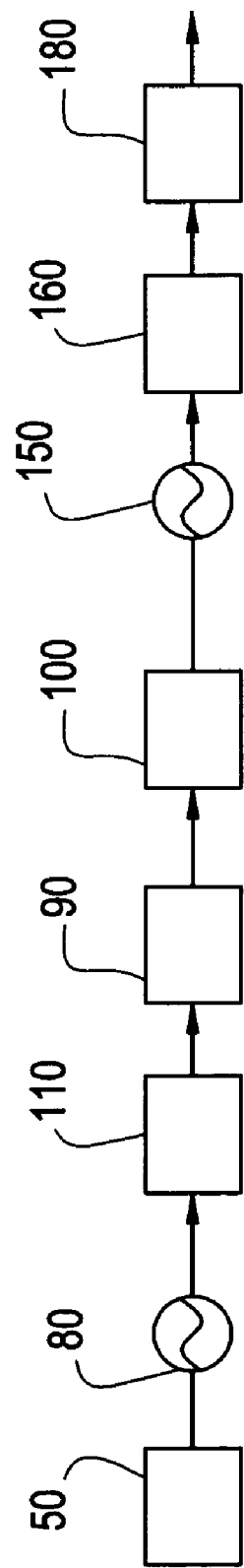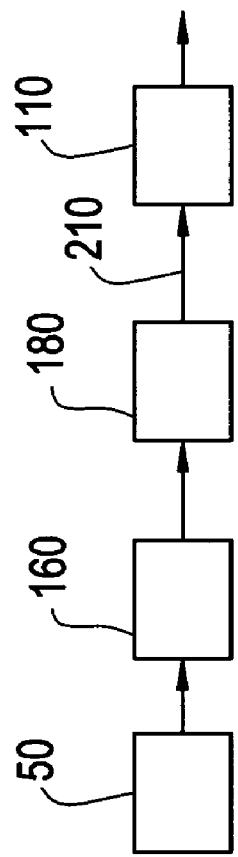

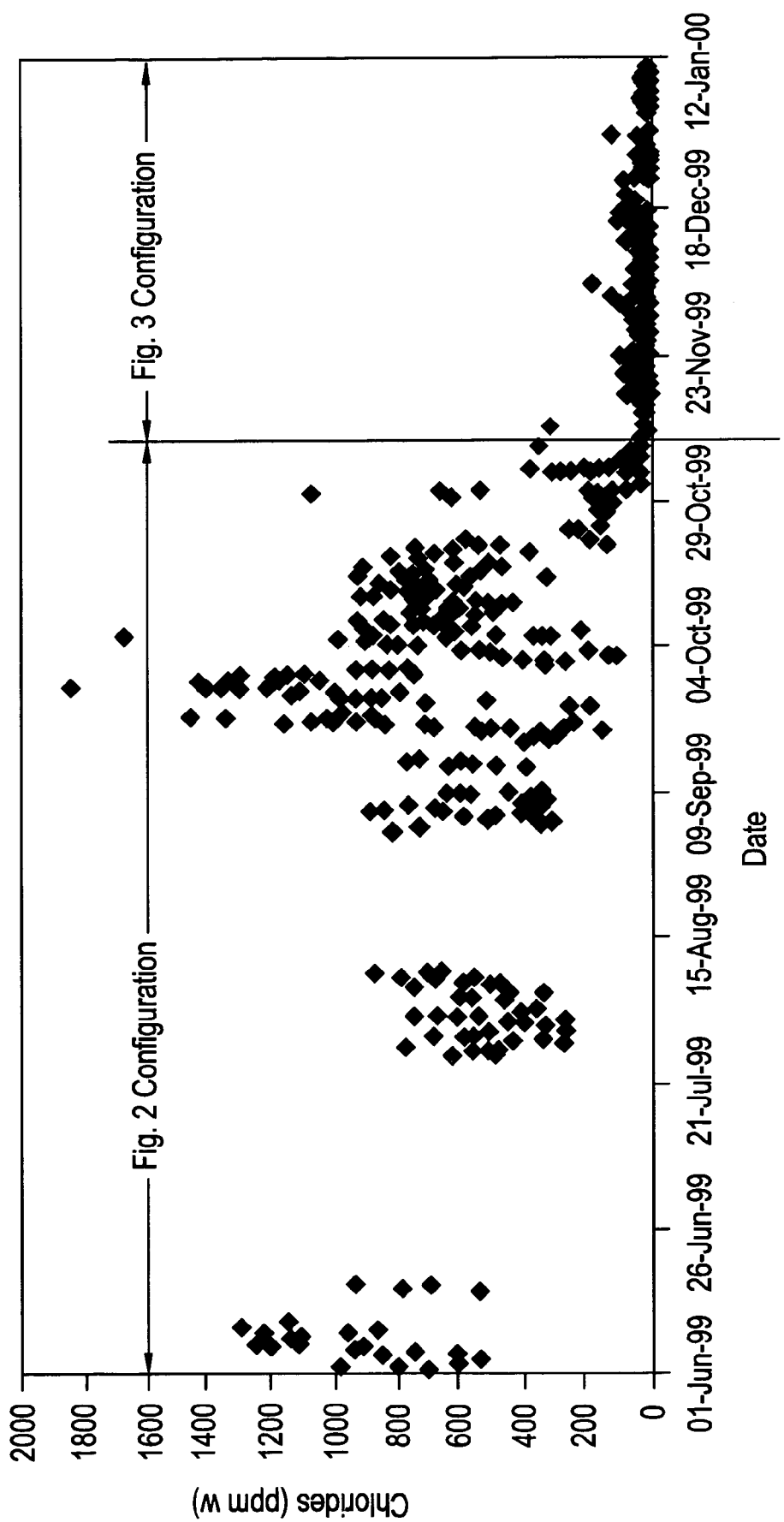

METHOD FOR PREPARING A DIALKYL CARBONATE, AND ITS USE IN THE PREPARATION OF DIARYL CARBONATES AND POLYCARBONATES

BACKGROUND OF INVENTION

Polycarbonate resins are useful materials valued for their physical and optical properties. Methods for the preparation of polycarbonate resins include interfacial processes and melt processes. In interfacial processes, as described, for example, in U.S. Pat. No. 4,360,659 to Sikdar, a bisphenol is reacted with phosgene in the presence of solvents. In melt processes, as described, for example, in U.S. Pat. No. 3,153,008 to Fox, a bisphenol is reacted with a diary carbonate. Melt processes are presently preferred because they avoid the use of phosgene and solvents.

Use of a melt process for polycarbonate synthesis requires an industrially efficient process for producing diaryl carbonates. There are several known processes for producing diaryl carbonates. One example of such a process is described by U.S. Pat. No. 4,182,726 to Illuminati et al. In this process, diaryl carbonates are produced by reacting dialkyl carbonates with aryl hydroxides (see Scheme I, below).

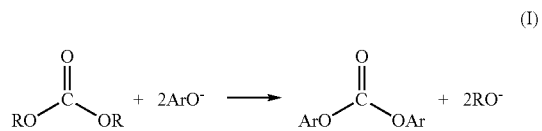
(I)

U.S. Pat. No. 4,182,726 also demonstrates that diary carbonates can be reacted together with dihydric phenols to produce polycarbonates (see Scheme II, below).

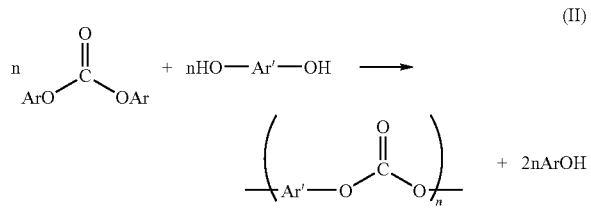
(II)

A preferred process for making dialkyl carbonates is illustrated in Scheme III, below, and described, for example, in U.S. Pat. No. 5,527,943 to Rivetti et al.; and U.S. Pat. Nos. 4,218,391 and 4,318,862 to Romano et al.

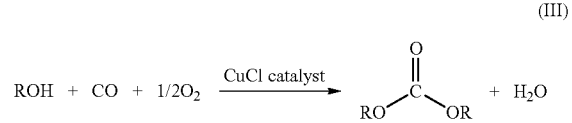
(III)

U.S. Pat. No. 5,527,943 (the '943 patent) also describes a known drawback of the dialkyl carbonate process according to Scheme (III): it produces water as a by-product. Also, hydrochloric acid (HCl) may be continuously added to the reaction mixture to maintain a desired molar ratio of chloride to copper. Therefore, HCl, CuCl catalyst, and water are typically found in the stream exiting the reactor vessel. Hydrochloric acid and copper chlorides are very corrosive in the presence of water, so equipment made from corrosion-resistant materials, such as glass-lined vessels, must be used in the reaction section of a chemical plant making dialkyl carbonates by this process. As corrosion-resistant equipment is expensive, there is a desire to use it in as little of the plant as possible.

A typical plant for performing preparing dialkyl carbonates according to Scheme Ill may contain three sections: a reaction section for converting raw materials to dialkyl carbonate, a separation section for isolating the dialkyl carbonate from unreacted monomers and by-products, and a purification section for removing water and further isolating the dialkyl carbonate. The '943 patent teaches that one can minimize the amount of corrosion-resistant equipment required by removing the HCl from the process stream immediately after the reaction section. This eliminates the necessity of using expensive corrosion-resistant materials in the separation and purification sections of the plant. The '943 patent further suggests that removal of HCl and possible copper halide salts from the stream immediately after the reaction section can be accomplished by exposing the gas-liquid mixture produced by the reaction to a liquid stream consisting of one of the process fluids. The '943 patent also states that the operating conditions employed are preferably adjusted such that the gaseous mixture from the reactor does not condense, or condenses only to a negligible extent, before the acid removal section in order to avoid the necessity of having to reheat the mixture before removing the HCl (col. 3, lines 17-30).

In view of the above, it was desirable to construct a plant wherein the HCl and any copper halide salts would be removed from the stream after the reaction section to avoid corrosion in the separation and purification sections. However, a technique similar to that described by the '943 patent—removing HCl and copper salts by treatment of a vaporized feed in a column using a counterflowing azeotrope fluid from the reaction mixture—failed to prevent corrosion in the downstream separation and purification sections.

There is therefore a need for a dialkyl carbonate process that recognizes and eliminates additional sources of corrosion.

SUMMARY OF INVENTION

The above-described and other drawbacks and disadvantages of the prior art are alleviated by a method of preparing a dialkyl carbonate, comprising: reacting an alkanol, oxygen, carbon monoxide, and a catalyst to form a mixture comprising a dialkyl carbonate, an alkyl chloroformate, hydrochloric acid, water, carbon dioxide, and carbon monoxide; and removing alkyl chloroformate from said mixture.

After considerable effort, the present inventors have discovered that dialkyl carbonate synthesis can form alkyl chloroformate by-products that lead to problematic corrosion. For example, in the reaction of methanol, carbon monoxide, and oxygen to form dimethyl carbonate (hereinafter "DMC"), methyl chloroformate (hereinafter "MCF") may be formed as a by-product. The MCF may pass through the HCl removal column into the separator and purification sections, where it reacts slowly with methanol and/or water to form corrosive HCl. Therefore, it was determined that steps were needed to remove MCF prior to the separation and purification sections.

Other embodiments, including an apparatus for preparing dialkyl carbonates, are described below.

BRIEF DESCRIPTION OF DRAWINGS

FIG. 2 is a simplified diagrammatic view of a comparative apparatus that is susceptible to corrosion.

FIG. 3 is a simplified diagrammatic view of an embodiment of the apparatus in which the fluid passageway 110 comprises two holding vessels 120.

FIG. 6 is a simplified diagrammatic view of an embodiment of the apparatus comprising an ion exchange resin bed 190.

FIG. 7 is a simplified diagrammatic view of an embodiment of the apparatus in which the fluid passageway 110 comprises a first gas-liquid separator 90 and a second gas-liquid separator 100.

FIG. 8 is a simplified diagrammatic view of an embodiment of the apparatus in which the fluid passageway 110 precedes the first gas-liquid separator 90.

FIG. 9 is a simplified diagrammatic view of an embodiment of the apparatus in which the fluid passageway 110 follows the azeotrope column 180.

FIG. 10 is a plot of chloride concentrations at the bottom of an azeotrope column 180 as a function of apparatus type (FIG. 2 and FIG. 3) and time.

DETAILED DESCRIPTION

One embodiment is a method, comprising: reacting an alkanol, oxygen, carbon monoxide, and a catalyst to form a mixture comprising a dialkyl carbonate, an alkyl chloroformate, hydrochloric acid, water, carbon dioxide, and carbon monoxide; and removing alkyl chloroformate from said mixture.

There is no particular limitation on the alkanol used in the method. Suitable alkanols include primary, secondary, and tertiary $C_1$-$C_{12}$ alkanols, with primary $C_1$-$C_6$ alkanols being preferred. Highly preferred alkanols include methanol.

Oxygen may be provided in any form, with gaseous forms being preferred. Suitable oxygen sources include, for example, air, and oxygen-containing gases having at least about 95 weight percent molecular oxygen, preferably at least about 99 weight percent molecular oxygen. Suitable oxygen-containing gases are commercially available from, for example, Air Products.

Carbon monoxide is preferably supplied as a gas having at least about 90 weight percent, preferably at least about 95 weight percent, more preferably at least about 99 weight percent, carbon monoxide. Suitable carbon monoxide-containing gases are commercially available from, for example, Air Products.

Suitable catalyst include those comprising iron, copper, nickel, cobalt, zinc, ruthenium, rhodium, palladium, silver, cadmium, rhenium, osmium, iridium, platinum, gold, mercury, and the like, and combinations comprising at least one of the foregoing metals. Preferred catalysts may comprise copper. A highly preferred catalyst comprises copper and chloride ion in a molar ratio of about 0.5 to about 1.5. Within this range, a molar ratio of at least about 0.8 may be preferred. Also within this range, a molar ratio of up to about 1.2 may be preferred. Highly preferred catalysts include cuprous chloride (CuCl) and cupric chloride ($CuCl_2$), with cuprous chloride being more highly preferred. During operation of the process, a suitable chloride ion concentration may be maintained by the addition of hydrochloric acid (HCl).

Figure 1:
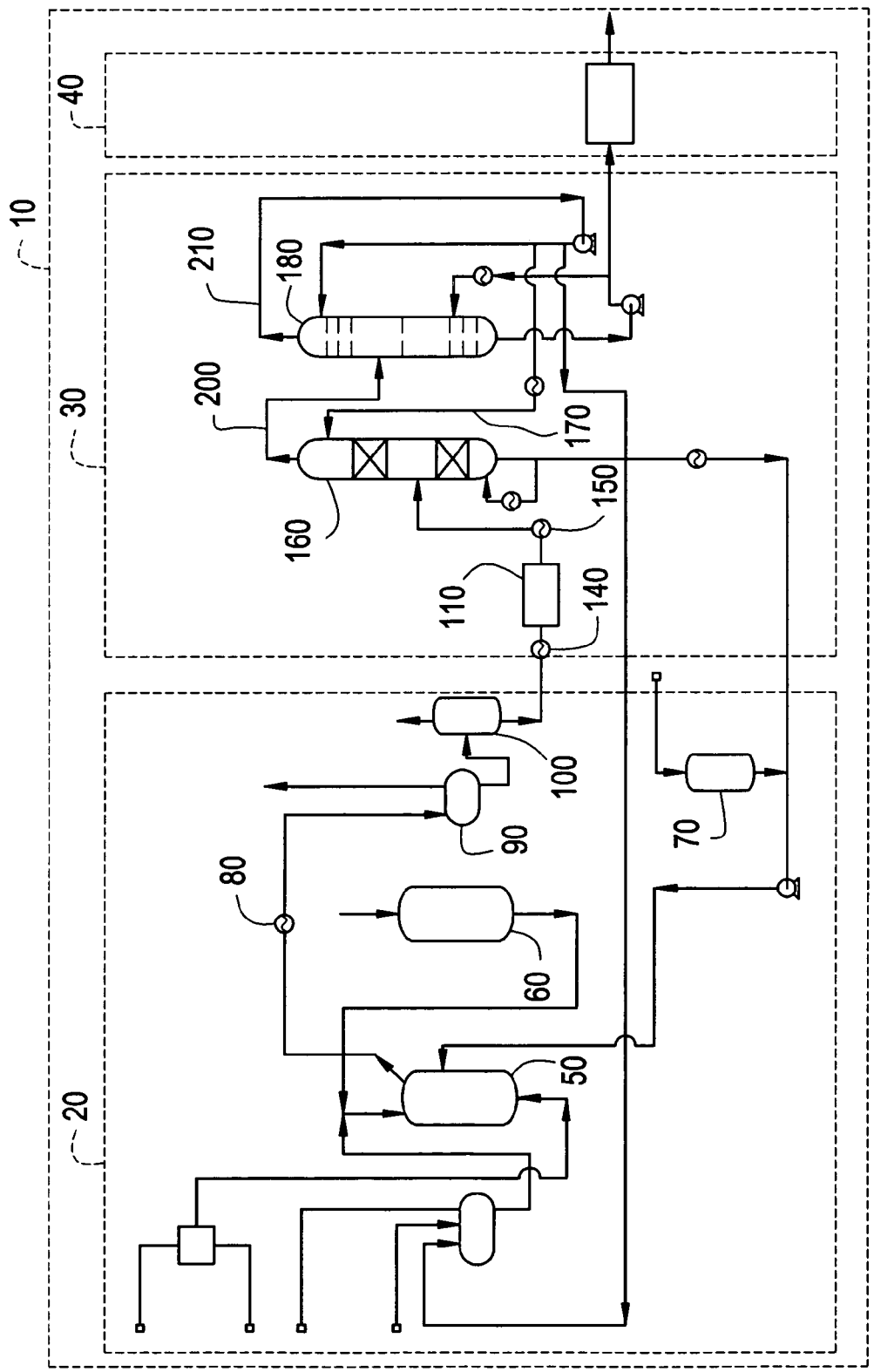
FIG. 1 is a diagrammatic view of a first embodiment of the apparatus.

FIG. 1 illustrates a dialkyl carbonate plant 10 having linked reaction section 20, separation section 30, and purification section 40. With reference to FIG. 1, the catalyzed reaction of alkanol, oxygen, and carbon monoxide may be performed in a single reactor 50, or in two or more reactors 50. The conditions for performing this step should be selected to maximize the yield of dialkyl carbonate while minimizing the degradation of dialkyl carbonate. Preferably, the reaction is performed in a single reactor 50, at a temperature of about 50° C. to about 250° C. Within this range, the temperature may preferably be at least about 100° C. Also within this range, the temperature may preferably be up to about 150° C. The reactor 50 is preferably kept at a pressure of about 15 to about 35 bar gauge (barg). Within this range, a pressure of at least about 20 barg may be preferred. Also within this range, a pressure up to about 28 barg may be preferred. In the case of dual reactor systems, the catalyst may be recycled between tanks. The catalyst concentration should be sufficiently high to produce an acceptable yield, but should be kept below a concentration that would cause solid setting of the catalyst in the reactor 50 or clogging of the equipment. The reactants alkanol, oxygen, and carbon monoxide are preferably added in a molar ratio of (about 0.5 to about 0.7):(about 0.04 to about 0.06):(about 0.8 to about 1.2), respectively. A highly preferred molar ratio of alkanol:oxygen:carbon monoxide is (about 0.6):(about 0.05):(about 1).

The amount of catalyst used relative to the reactants will depend on the identity of the catalyst. For example, when the catalyst comprises CuCl, a highly preferred catalyst concentration is about 140 to about 180 grams per liter of reaction mixture. During operation, the catalyst may initially be added from a catalyst tank 60. Sufficient HCl is preferably added to reactor 50 from a hydrochloric acid tank 70 during the course of the reaction to maintain a molar ratio of Cu:Cl close to 1.0. The concentration of HCl is preferably continuously determined and controlled by the addition of HCl. A typical mass ratio for HCl feed to total liquid feed is about $6 \times 10^{-4}$ to about $8 \times 10^{-4}$.

The reaction produces a mixture comprising a dialkyl carbonate, an alkyl chloroformate, hydrochloric acid, water, carbon dioxide, and carbon monoxide. The mixture may further comprise residual methanol and oxygen, as well as side-products such as alkyl chlorides and dialkyl ethers. The mixture is typically withdrawn from the reactor 50 in a gas/vapor form. The term "vapor" is meant to refer to gaseous organic components of the mixture such as, for example, evaporated dialkyl carbonates, alcohols, alkyl chloroformates, etc., and to water vapor. That is, the term "vapor" refers to fluids having a boiling point of at least −50° C. at one atmosphere. In contrast, the term "gas" is meant to refer to the gaseous oxygen, carbon dioxide, carbon monoxide, and optional nitrogen. That is, the term "gas" refers to fluids having a boiling point less than −50° C. at one atmosphere. The vapor may be at least partially condensed in condenser 80, and fed to a first gas-liquid separator 90. The apparatus may optionally employ a single gas-liquid separator, or a plurality of (i.e., at least 2; preferably up to about 5) gas-liquid separators. The first gas-liquid separator 90 may be kept at a pressure within about 10%, more preferably within about 1%, of the pressure of the reactor 50. The gas effluent from the first gas-liquid separator 90 may be recycled, for example to reuse excess carbon monoxide. The mixture may be sent to a second gas-liquid separator 100, which preferably has a pressure less than about 20% of the pressure of the reactor 50 (e.g., preferably less than 3 bar gauge, more preferably about 0.2 bar gauge) to preferably achieve separation of at least about 90%, more preferably at least 95%, by weight of the remaining gas in the mixture. In a highly preferred embodiment, substantially all of the gas is removed from the mixture. The gas effluent removed from the second gas-liquid separator 100 can also be recycled. It is preferred that the vapor in the mixture be in a partially condensed form (i.e., at least about 10% condensed), more preferably a fully condensed form (i.e., at least about 90% condensed), before entering the first gas-liquid separator 90, and between the first gas-liquid separator 90 and the second gas-liquid separator 100.

In the embodiment shown in FIG. 1, the mixture exiting the second gas-liquid separator 100 may be in a single liquid phase. After the second gas-liquid separator 100, the mixture may proceed through a fluid passageway 110 that removes alkyl chloroformate from the mixture. It will be understood that the terms "remove" and "removal" in reference to a particular chemical species encompass any chemical or physical process that reduces the concentration of the species in the mixture. The alkyl chloroformate may be removed from the condensate by any method. Some preferred methods include heating, increasing pressure, increasing residence time, adding a polar solvent, adsorbing, separating with a membrane (including gas and liquid membrane separation), pervaporating, passing through an ion exchange resin, exposing to a stoichiometric reagent, exposing to a catalytic reagent, and the like, and combinations comprising at least one of the foregoing techniques. In a preferred embodiment, the alkyl chloroformate is removed from mixture by reaction with water (see Scheme IV) or alkanol (see Scheme V).

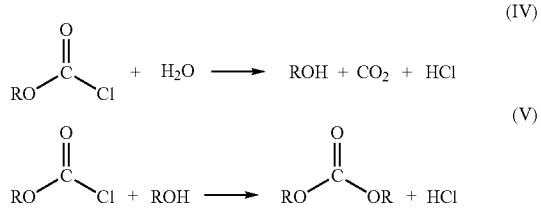

It may also be preferred to remove the alkyl chloroformate without passing the mixture through an ion exchange resin, because such resins are expensive to install and operate. It may be preferred to remove at least about 50 percent, more preferably at least about 90 percent, yet more preferably at least about 95 percent, even more preferably at least about 99 percent, of the alkyl chloroformate from the mixture. In one embodiment, it may be preferred to reduce the alkyl chloroformate concentration in the mixture to less than about 500 ppm, more preferably less than about 100 ppm, yet more preferably less than about 30 ppm. In any of these embodiments, it may be preferred to remove less than about 10%, more preferably less than about 5%, yet more preferably less than about 1%, of the dialkyl carbonate. Although the method may be described as "removing less than about 10% of said dialkyl carbonate", it will be understood that the concentration of dialkyl carbonate need not be reduced and may even increase. For example, the concentration of dialkyl carbonate may increase if the Scheme V reaction of alkyl chloroformate with methanol forms dialkyl carbonate faster than dialkyl carbonate decomposes due to other reactions.

Through extensive kinetic studies of the dimethyl carbonate process utilizing variations in factors including temperature, residence time, water concentration, methanol concentration, and hydrochloric acid concentration, the present inventors have found that the rate of methyl chloroformate decomposition may be given by the equation (1)

$$-r_{MCF} = (k_1[H_2O] + k_2[MeOH])[MCF] \qquad (1)$$

where $r_{MCF}$ is the rate of change of the moles of methyl chloroformate (MCF) per unit volume, $[H_2O]$, $[MeOH]$, and $[MCF]$ are the instantaneous concentrations of water, methanol, and methyl chloroformate, respectively, in moles per unit volume, and $k_1$ and $k_2$ are rate constants that vary with temperature according to equations (2) and (3), respectively $$k_1 = k_1^0 e^{-6381/T} \qquad (2)$$

$$k_2 = k_2^0 e^{-7673/T} \qquad (3)$$

where $k_1^0 = 2.09 \times 10^9$ mL/mol–min, $k_2^0 = 4.14 \times 10^{10}$ mL/mol–min, and T is the temperature in degrees kelvin.

In many cases, it is valid to assume that the concentrations of water and methanol, and the density of the solution are essentially constant. Within these general kinetic constraints, different kinetic expressions may be used for different process and apparatus types. With knowledge of the relevant chemical reactions and rate constants provided in this application, these expressions may be readily derived by those of ordinary skill in the art. For example, in a batch process, the rate of methyl chloroformate decomposition may be expressed as a function of residence time, as shown in equation (4):

$$-d[MCF]/dt = (k_1[H_2O] + k_2[MeOH])[MCF] \qquad (4)$$

where t is residence time in minutes. The residence time t may be defined as the total time spent by an average molecule in the fluid passageway 110. In a batch process, at least about 50% of the methyl chloroformate may be removed by maintaining the mixture under conditions comprising a water concentration ($[H_2O]$), a methanol concentration ($[MeOH]$), a temperature (T), and a residence time (t), such that a parameter X according to the equation (5)

$$X = exp\{-[(2.09 \times 10^9) e^{(-6381/T)} [H_2O] + (4.14 \times 10^{10}) e^{(-7673/T)} [MeOH]] t\} \qquad (5)$$

has a value less than about 0.9, wherein the water concentration and the methanol concentration are expressed in moles per milliliter, the temperature is expressed in degrees Kelvin, and the residence time is expressed in minutes. The value of X may preferably be less than about 0.5, more preferably less than about 0.2, yet more preferably be less than about 0.1, even more preferably less than about 0.05, still more preferably less than about 0.01. The water concentration may be about 0.1 to about 50 moles per liter (mol/L). Within this range, the water concentration may preferably be at least about 0.5 mol/L, more preferably at least about 1 mol/L. Also within this range, the water concentration may preferably be up to about 30 mol/L, more preferably up to about 20 mol/L, yet more preferably up to about 10 mol/L, even more preferably up to about 5 mol/L. The methanol concentration may be about 1 to about 25 mol/L. Within this range, the methanol concentration may preferably be at least about 5 mol/L, more preferably at least about 10 mol/L. Also within this range, the methanol concentration may preferably be up to about 20 mol/L, more preferably up to about 18 mol/L. The residence time may be about 0.5 hour to about 10 hours. Within this range, the residence time may preferably be at least about 1 hours, more preferably at least about 2 hours. Also within this range, the residence time may preferably be up to about 8 hours, more preferably up to about 6 hours. The temperature may be about 30 to about 130° C. Within this range, the temperature may preferably be at least about 40° C., more preferably at least about 50° C., yet more preferably at least about 60° C. Also within this range, the temperature may preferably be up to about 110° C., more preferably up to about 100° C., yet more preferably up to about 90° C.

In the limit of an ideal steady state plug flow reactor, and assuming constant density of the mixture, the rate of methyl chloroformate decomposition may be expressed according to equation (3), with t representing residence time in minutes.

For an ideal steady state continuous stirred tank reactor (CSTR), the concentration of methyl chloroformate is given by equation (6)

$$[MCF] = [MCF]_{t=0}(1/(1+kt)) \quad (6)$$

where $[MCF]_{t=0}$ is the initial concentration of methyl chloroformate in moles per milliliter, t is the residence time in minutes, and k is given by equation (7)

$$k = k_1[H_2O] + k_2[MeOH] \quad (7)$$

where $k_1$, $k_2$, $[H_2O]$, and $[MeOH]$ are as defined above.

In another embodiment that relates to a batch reactor, removing alkyl chloroformate from the mixture comprises maintaining the mixture under conditions comprising an initial concentration of methyl chloroformate ($[MCF]_{t=0}$), a water concentration ($[H_2O]$), a methanol concentration ($[MeOH]$), a temperature (T), and a residence time (t), such that a parameter Z calculated according to the equation (8)

$$Z = [MCF]_{t=0} \exp\{-[(2.09 \times 10^9) e^{(-6381/T)}[H_2O] + (4.14 \times 10^{10}) e^{(-7673/T)}[MeOH]]t\} \quad (8)$$

has a value less than about $5 \times 10^{-6}$, preferably less than about $1 \times 10^{-6}$, more preferably less than about $5 \times 10^{-7}$, even more preferably less than about $5 \times 10^{-8}$, wherein the initial concentration of methyl chloroformate, the water concentration, and the methanol concentration are expressed in moles per milliliter, the temperature is expressed in degrees Kelvin, and the residence time is expressed in minutes. The temperature, residence time, methanol concentration, and water concentration in this expression are as described above. The initial concentration of methyl chloroformate will depend on the reactor conditions, but it is typically about $5 \times 10^{-3}$ moles per liter to about $5 \times 10^{-1}$ moles per liter. Within this range, the initial concentration of methyl chloroformate may be at least about $1 \times 10^{-2}$ moles per liter. Also within this range, the initial concentration of methyl chloroformate may be up to about $1 \times 10^{-1}$ moles per liter.

In a preferred embodiment that relates to a batch reactor, removing alkyl chloroformate comprises subjecting the mixture to conditions comprising an initial dimethyl carbonate concentration ($[DMC]_{t=0}$), an initial water concentration ($[H_2O]_{t=0}$), an initial methanol concentration ($[MeOH]_{t=0}$), an initial hydrochloric acid concentration ($[HCl]_{t=0}$), a temperature (T), and a residence time (t), such that a parameter X calculated according to the equation (9)

$$X = \exp\{-[(2.09 \times 10^9) e^{(-6381/T)}[H_2O]_{t=0} + (4.14 \times 10^{10}) e^{(-7673/T)}[MeOH]_{t=0}]t\} \quad (9)$$

has a value less than about 0.9, and a parameter Y calculated according to the equation (10)

$$Y = \frac{\left(1 - \frac{[H_2O]_{t=0}}{[DMC]_{t=0}}\right)}{\left(1 - \left(\frac{[H_2O]_{t=0}}{[DMC]_{t=0}}\right)\left(\exp\left((6.6 \times 10^{10})(\exp(-6636/T))[HCl]_{t=0}[DMC]_{t=0}\left(\frac{[H_2O]_{t=0}}{[DMC]_{t=0}} - 1\right)t\right)\right)\right)} \quad (10)$$

has a value of at least about 0.9, wherein the initial dimethyl carbonate concentration, the initial water concentration, the initial methanol concentration, and the initial hydrochloric acid concentration are expressed in moles per milliliter, the temperature is expressed in degrees Kelvin, and the residence time is expressed in minutes. The value of Y may preferably be at least about 0.95, more preferably at least about 0.99. Suitable analytical techniques to determine initial concentrations of water, methanol, hydrochloric acid, and dimethyl carbonate in reaction mixtures are well known in the art. The term "initial concentration" refers to the concentration of a species before intentional removal of alkyl chloroformate. The initial water and methanol concentrations are the same as the water and methanol concentrations described above (under typical reaction conditions, the water and methanol concentrations are large are essentially constant during alkyl chloroformate removal). The initial dimethyl carbonate concentration may be about 0.5 to about 10 mol/L. Within this range, the initial dimethyl carbonate concentration may preferably be at least about 1 mol/L, more preferably at least about 2 mol/L. Also within this range, the initial dimethyl carbonate concentration may preferably be up to about 8 mol/L, more preferably up to about 6 mol/L. The concentration of HCl in the mixture will depend on the type and concentration of catalyst employed. The initial hydrochloric acid concentration will depend on the type and amount of catalyst, but it is typically about $1 \times 10^{-3}$ to about $2 \times 10^{-1}$ moles per liter. Within this range, the initial hydrochloric acid concentration may preferably be at least about $5 \times 10^{-1}$ more preferably at least about $1 \times 10^{-2}$ mol/L. Also within this range, the initial hydrochloric acid concentration may preferably be up to about $1 \times 10^{-1}$ more preferably up to about $7 \times 10^{-2}$ mol/L.

The method may be operated, for example, in a batch, semi-batch, or continuous manner.

In the particular embodiment shown in FIG. 1, the mixture passes through a first heat exchanger 140 to adjust the temperature of the mixture about 30° C. to about 130° C. Within this range, the temperature may preferably be at least about 40° C., more preferably at least about 50° C. Also within this range, the temperature may preferably be up to about 80° C., more preferably up to about 70° C. The term "heat exchanger" describes a well-known device for heating chemical reaction streams, typically by exchanging heat between a thermal energy source (e.g., steam) and a cooler chemical reaction stream, but it is understood that other types of equivalent heaters (e.g., electrical heaters) are also included. The condensate may proceed into a fluid passageway 110, which serves to increase the residence time of the mixture under conditions to maximize decomposition of alkyl chloroformate while minimizing decomposition of dialkyl carbonate. The condensate may preferably remain fully condensed within the fluid passageway 110. It is desirable to keep the condensate fully condensed because at least some alkyl chloroformates (e.g., methyl chloroformate) are more stable in the vapor phase than the liquid phase under conditions used for this process.

Figure 4:
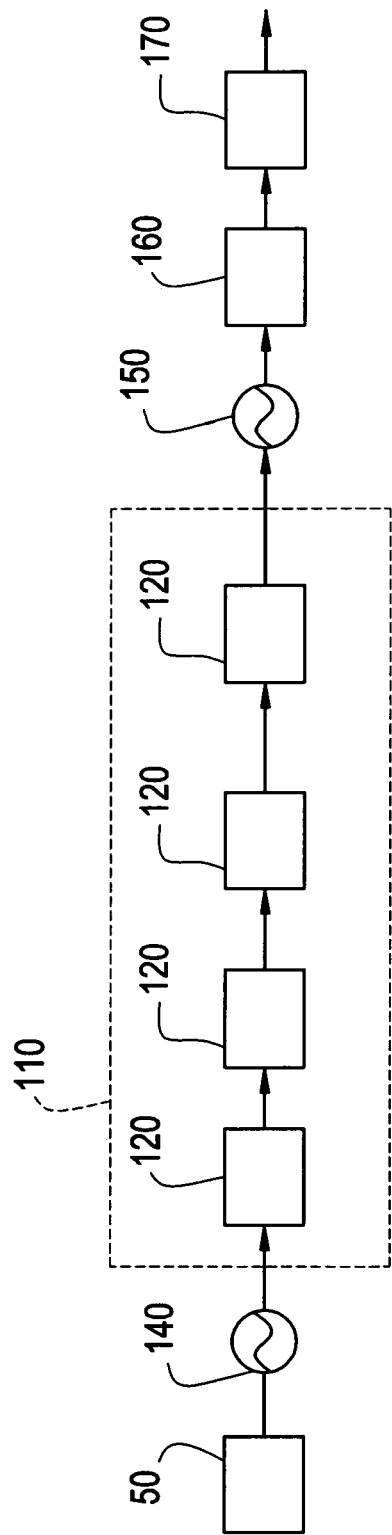
FIG. 4 is a simplified diagrammatic view of an embodiment of the apparatus in which the fluid passageway 110 comprises four holding vessels 120.
Figure 5:
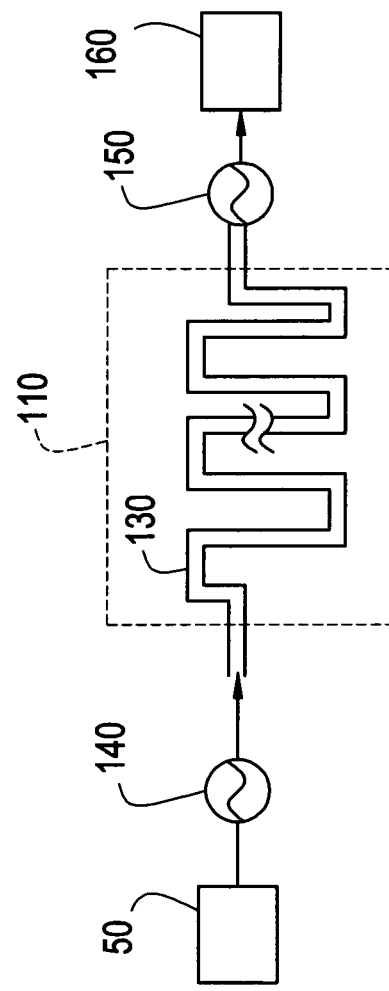
FIG. 5 is a simplified diagrammatic view of an embodiment of the apparatus in which the fluid passageway 110 comprises a tubular section 130.

The residence time and temperature in the fluid passageway 110 are preferably sufficient to remove enough alkyl chloroformate to prevent unacceptable downstream corrosion, but they should not be so excessive as to cause unnecessary reductions in the productivity and yield of the desired dialkyl carbonate product. FIG. 2 shows a simplified process diagram representative of a comparison process. In this process, the mixture flows directly from a first gas-liquid separator 90 to a first heat exchanger 140, then to an acid removal column 160. Three specific embodiments of the fluid passageway 110 are shown in FIGS. 3, 4, and 5. In a preferred embodiment, at least about 50% of the alkyl chloroformate is removed, more preferably at least 80% is removed. In a highly preferred embodiment, the alkyl chloroformate concentration is reduced to less than about 500 parts per million (ppm) by weight, more preferably less than about 100 ppm by weight, yet more preferably less than about 30 ppm by weight, based on the total weight of the mixture after alkyl chloroformate removal. The fluid passageway 110 is preferably selected such that the total residence time between the reactor 50 and the acid removal column 160 is about 0.5 hour to about 10 hours. Within this range, the residence time may preferably be at least about 1 hour, more preferably at least about 2 hours. Also within this range, the residence time may preferably be up to about 8 hours, more preferably up to about 7 hours.

In one embodiment, illustrated in FIG. 3, the fluid passageway 110 comprises 2 holding vessels 120. These holding vessels 120 may, for example, maintain the mixture at a temperature of about 55° C. for about 2 hours. Each holding vessel 120 may preferably have a length to volume ratio (L/V) less than 5, preferably less than about 2. While two holding vessels 120 are illustrated in this figure, there is no particular limitation on the number of holding vessels 120 in the fluid passageway 110. It may be preferred to use at least 2 holding vessels 120, and configurations comprising 3, 4, 5, 6, or more holding vessels 120 may also be preferred.

In another embodiment, illustrated in FIG. 4, the fluid passageway 110 comprises 4 holding vessels 120. These holding vessels 120 may, for example, maintain the mixture at a temperature of about 70° C. for about 4 hours. Each holding vessel 120 may preferably have a length to volume ratio (L/V) less than 5, preferably less than about 2.

In yet another embodiment, illustrated in FIG. 5, the fluid passageway 110 may comprise a section having L/V of at least 5, preferably at least about 10. For brevity, this section may be referred to as a tubular section 130. Such a tubular section 130 having L/V>5 may promote plug flow of the mixture through the fluid passageway 110, thereby efficiently utilizing the residence time for removal of the alkyl chloroformate. In this embodiment, it may be preferred that the mixture reside in one or more narrow sections having L/V>5 for at least about 50% of the total residence time spent in the fluid passageway 110, more preferably at least about 80% of the total residence time spent in the fluid passageway 110.

Referring again to FIG. 1, after exiting the fluid passageway 110, the mixture may, optionally, pass through a second heat exchanger 150 to at least partially vaporize the mixture. This second heat exchanger 150 may have a residence time of less than 10 minutes. This vaporization step may also be accomplished without a heat exchanger by lowering the pressure applied to the condensed mixture (e.g., bypassing the condensate into an acid removal column 160 that is kept at a relatively lower pressure). The vaporized mixture may then, optionally, be treated to remove HCl, preferably by injecting it into an acid removal column 160. The acid removal column 160 may also help remove any entrained catalyst (e.g., CuCl) that could otherwise contribute to downstream corrosion. In the acid removal column 160, the vaporized condensate may preferably encounter a counter-flowing liquid supplied by counter-flowing liquid line 170 to a higher point in the column (e.g., the upper third). The counter-flowing liquid may trap the remaining HCl and other reactants, which may be removed from the bottom of the acid removal column 160 and recycled to the reactor 50. The dialkyl carbonate mixture may be removed from the top of the acid column 160 via exit line 200, and, optionally, passed into an azeotrope column 180. As shown in FIG. 6, an optional ion exchange resin bed 190 may be included after the acid removal column 160, or at any other position downstream with respect to the acid removal column 160. It may be advantageous to include an optional ion exchange resin bed 190 after water is removed from the product dialkyl carbonate stream in the purification section 40. In a preferred embodiment, the apparatus does not include an ion exchange resin bed 190.

In a preferred embodiment, the method comprises reducing the concentration of hydrochloric acid in the mixture to less than about $1 \times 10^{-3}$ mol/L, more preferably less than about $5 \times 10^{-4}$ mol/L, even more preferably less than about $1 \times 10^{-4}$ mol/L, based on the total composition after removing hydrochloric acid.

In a preferred embodiment, the portions of the separation section 30 downstream from the azeotrope column 180, and the purification subsection 40 are not required to be corrosion-resistant. Equipment upstream of the azeotrope column 180 is preferably corrosion-resistant; for example, it may be glass lined. The term "corrosion-resistant" is meant to describe a material capable of withstanding an HCl content of 500 ppm at a temperature of about 50° C. to about 135° C. in the reaction mixture without substantial corrosion in a relatively brief time period (e.g., six months). Glass lined vessels, precious metal (e.g., tantalum) lined vessels and special steels such as HASTELLOY® and CHROMALLOY® would be considered corrosion-resistant materials, while ordinary stainless steels not modified to enhance corrosion resistance would not be considered corrosion-resistant. The azeotrope column 180 can be made at least in part from corrosion-resistant metals. In a preferred embodiment, the bottom of the azeotrope column 180 may be made from a corrosion-resistant steel, whereas the top of the column can be ordinary stainless steel.

In one embodiment of the apparatus, illustrated in FIGS. 1 and 3-6, alkyl chloroformate is removed in a fluid passageway 110.

In another embodiment of the apparatus, illustrated in FIG. 7, the mixture is present in the gas-liquid separation vessels 90 and 100 for sufficient residence time and at sufficient temperature to remove alkyl chloroformate. In other words, the fluid passageway 110 comprises the gas-liquid separation vessels 90 and 100. For example, the mixture may remain in the condense phase in the gas-liquid separation vessels to be substantially decomposed by reactions with water and methanol. In this embodiment, the first heat exchanger 140 and the holding vessels 120 may be unnecessary.

In another embodiment of the apparatus, illustrated in FIG. 8, the alkyl chloroformate may be removed in a fluid passageway 110 that precedes the gas-liquid separation vessels 90 and 100. In this embodiment, one of the above-mentioned techniques for removing alkyl chloroformate may be employed upstream of the gas-liquid separation vessels 90 and 100.

In another embodiment of the apparatus, illustrated in FIG. 9, the hydrochloric acid may be removed from the mixture before removing the alkyl chloroformate. In this embodiment, the alkyl chloroformate may be removed in the vapor, rather than the liquid phase. For example, referring to FIG. 9, the fluid passageway 110 may follow the azeotrope column 180; for example, it may be inserted into the azeotrope column vapor exit line 210. In this embodiment, the first heat exchanger 140 and the holding vessels 120 illustrated in FIG. 3 may be omitted. In this embodiment, the fluid passageway 110 may preferably comprise an apparatus suitable for removing alkyl chloroformate from the vapor phase (e.g., ion exchange resins, absorption beds, vapor phase membranes, etc.), and the alkyl chloroformate need not be condensed.

A preferred embodiment is a method of preparing a dialkyl carbonate, comprising: reacting an alkanol, oxygen, carbon monoxide, and a catalyst to form a mixture comprising a dialkyl carbonate, an alkyl chloroformate, hydrochloric acid, water, carbon dioxide, and carbon monoxide; and passing said mixture through a fluid passageway 110 at a temperature of about 50° C. to about 80° C. and for a residence time of about 1 hour to about 10 hours.

Another preferred embodiment is an apparatus for preparing a dialkyl carbonate, comprising: means for reacting an alkanol, oxygen, carbon monoxide, and a catalyst to form a mixture comprising a dialkyl carbonate, an alkyl chloroformate, hydrochloric acid, water, carbon dioxide, and carbon monoxide; and means for removing alkyl chloroformate from said mixture.

Another preferred embodiment is an apparatus for preparing a dialkyl carbonate, comprising: a reactor for reacting an alkanol, oxygen, carbon monoxide, and a catalyst to produce a mixture comprising a dialkyl carbonate, an alkyl chloroformate, hydrochloric acid, water, and carbon dioxide; and a fluid passageway 110 for removing alkyl chloroformate.

Dialkyl carbonates prepared according to the method are useful for the preparation of diaryl carbonates. For example, diaryl carbonates may be generated by the reaction of a dialkyl carbonate with an aryl hydroxide (see Scheme I, above). The diaryl carbonate may in turn be reacted with a dihydric phenol to form a polycarbonate (see Scheme II, above). For example, dimethyl carbonate prepared according to the method may be reacted with phenoxide to form diphenyl carbonate, which in turn may be reacted with bisphenol A to form a polycarbonate.

The invention is further illustrated by the following non-limiting examples.

EXAMPLE 1

A plant according to simplified FIG. 2 was built and operated to produce dimethyl carbonate. Corrosion damage was observed in and downstream of the azeotropic column 180. After extensive experimentation, it was determined that the corrosion damage was caused by methyl chloroformate passing through the acid separation column. Specifically, methyl chloroformate was found to be present in the azeotrope column 180 at a concentration of 300 parts per million (ppm) by weight.

EXAMPLES 2-5

The decomposition kinetics of methyl chloroformate were studied under four different conditions. A procedure for determining methyl chloroformate in a sample was as follows. For Example 2, 32 milliliters (mL) of dimethyl carbonate, 10 mL of dimethyl carbonate containing 50 mg of a biphenyl internal standard 63 mL of methanol, and 5 ml of water were added to a 250 mL flask equipped with a thermometer, a condenser, and a port for sampling. (Toluene may be used instead of the methanol/water solution.) The resultant homogeneous solution was placed in an oil bath and the temperature of the solution was held constant at 50° C. At time zero, 81.7 microliters of pure methyl chloroformate were added to the solution (1,000 ppm on a weight basis). Samples were withdrawn at various time intervals and were quenched by reacting the methyl chloroformate in the sample with diisobutyl amine to convert the methyl chloroformate to N,N'-diisobutyl methyl carbamate. The amount of N,N'-diisobutyl methyl carbamate was then analyzed via titration with a standard silver nitrate solution to quantify the amount of ionic chloride present. The amount of methyl chloroformate could then be inferred by analyzing the original sample for ionic chloride. The difference in chloride concentration is equal to the methyl chloroformate concentration because each equivalent of methyl chloroformate liberates one equivalent of ionic chloride upon derivatization. Alternatively, gas chromatography can be used for direct analysis of the N,N'-diisobutyl methyl carbamate using an internal standard.

Table 1 below show the observed decomposition rate constants (k) at 50° C. for various conditions. Example 2 corresponds to the case described above. Example 3 has added hydrochloric acid that is generally present in the authentic reaction mixture. In Example 4, the effect of a small amount of sodium bicarbonate was tested. In Example 5, the ratio of dimethyl carbonate to methanol was held constant, but the amount of water was increased from 5% to 10%. The results are summarized below in Table 1.

[t4]

TABLE I

|  | DMC (wt %) | MeOH (wt %) | $H_2O$ (wt %) | Temp (° C.) | k (min$^{-1}$) |
|---|---|---|---|---|---|
| Ex. 2 | 45 | 50 | 5 | 50 | 0.043 |
| Ex. 3* | 45 | 50 | 5 | 50 | 0.043 |
| Ex. 4** | 45 | 50 | 5 | 50 | 0.480 |
| Ex. 5*** | 43 | 47 | 10 | 50 | 0.055 |

*Identical to Ex. 2, except that it also had 1000 ppm of HCl, which is similar to the effluent from the reactor 50.
**Identical to Ex. 2, except that 1.6 eq. of NaHCO$_3$ relative to the 1000 ppm MCF were added.
***Identical to Ex. 2, except that the % water was increased by 10%, but the ratio of DMC/MeOH was not changed, just reduced overall Plots of the logarithm of methyl chloroformate concentration versus time were linear, fitting a pseudo-first-order kinetic model. This behavior was observed even in the presence of hydrochloric acid, and therefore this method can be used to determine the concentration of methyl chloroformate in a particular sample. Comparison of Examples 2 and 5 indicates that only minor variations in the rate coefficient, k, are observed when analyzing samples having water contents varying by a factor of two. Comparison of Examples 2 and 3 shows, surprisingly, that added HCl did not affect the observed rate of methyl chloroformate decomposition. Comparison of Examples 2 and 4 shows that even a small amount of base increased the reaction rate by more than ten-fold. As a practical matter, however, it may be desirable to avoid strongly basic conditions because they also may increase the decomposition rate of dimethyl carbonate.

EXAMPLE 6, COMPARATIVE EXAMPLE 1

These experiments show that the fluid passageway 110 is effective to reduce the concentration of methyl chloroformate that can react to form HCl in downstream sections of the plant. With reference to FIG. 1, two samples were obtained by sampling the process fluid at different points in a dimethyl carbonate plant having a configuration with a first heat exchanger 140 and two holding vessels 120 (i.e., a configuration corresponding to FIG. 3). The first sample (Comparative Example 1) was taken immediately before the first heat exchanger 140. The second sample (Example 6) was taken after the second holding vessel 120 (i.e., after the fluid passageway 110). Each same was taken to the lab, and its chloride content was determined as a function of time elapsed from sampling. The results are presented in Table II. The Ex. 6, data show essentially constant levels of chloride ion, indicating that labile, chloride-generating species such as methyl chloroformate are not present in the sample. In contrast, the data for Comp. Ex. 1 show an increase with chloride level over time, consistent with presence of methyl chloroformate in the initial sample and its decomposition over time to form additional chloride ion. Thus, the data collectively show that in the absence of the fluid passageway 110, substantial chloride formation may take place in downstream (post-acid removal column 160) sections of the plant, causing corrosion, but the presence of the fluid passageway 110 is effective to decompose alkyl chloroformate to chloride ion before the acid removal column 160, thereby preventing downstream corrosion.

TABLE II

| | Chloride Concentration (ppm) | |
|---|---|---|
| Time (h) | Ex. 6 | Comp. Ex. 1 |
| 0 | 374 | 189 |
| 2 | 408 | 312 |
| 4 | 374 | 339 |
| 8 | 372 | 368 |
| 10 | 372 | 357 |
| 25 | 381 | 368 |

EXAMPLE 7, COMPARATIVE EXAMPLE 2

Figure 11:
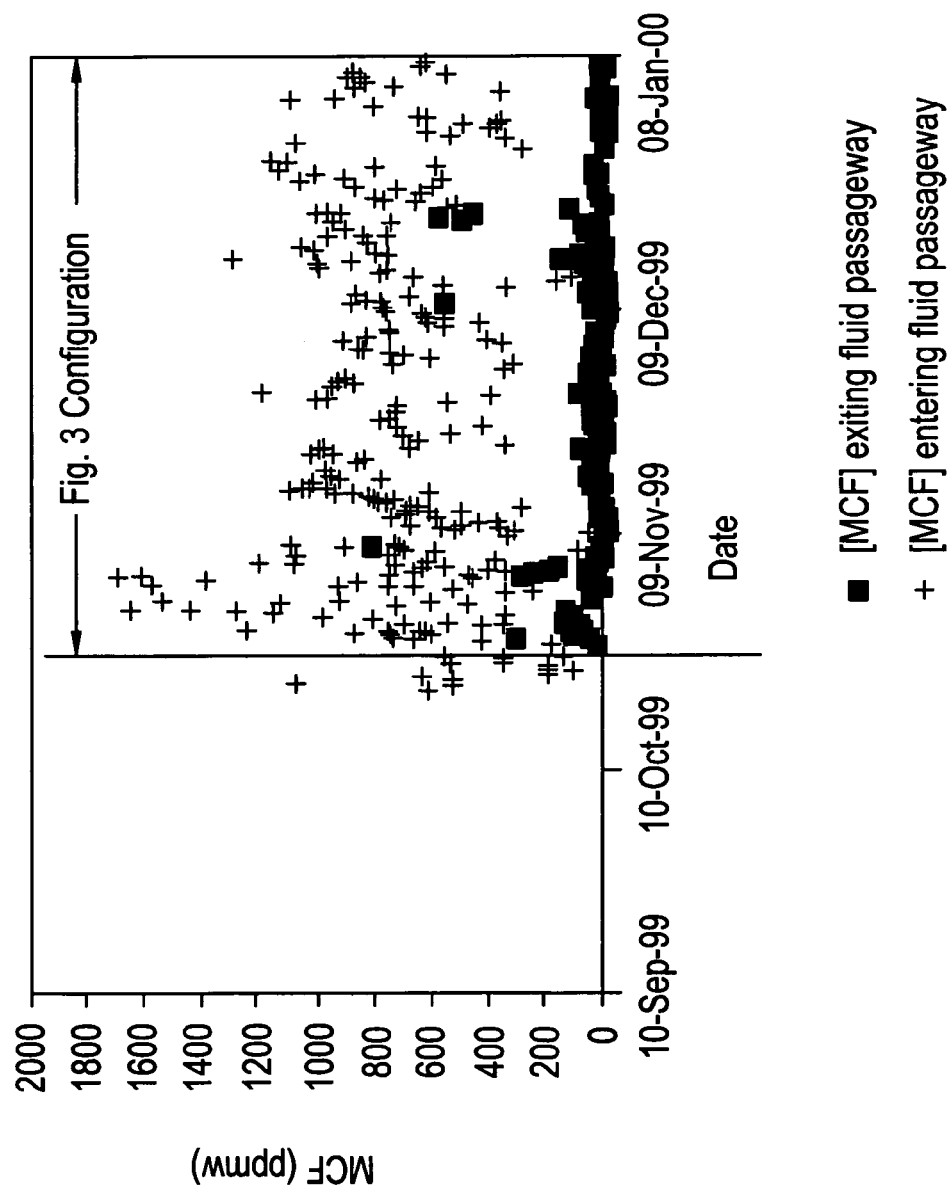
FIG. 11 is a plot of methyl chloroformate concentrations entering and exiting the fluid passageway 110 as a function of time for an apparatus corresponding to FIG. 3.

For Comparative Example 2, a dimethyl carbonate plant according to simplified FIG. 2 was operated according to the conditions described in Table III, below. This plant was similar to that shown in more detail in FIG. 1, with the exception that the first heat exchanger 140 and the fluid passageway 110 were absent. Corrosion was observed in and downstream of the azeotrope column 180. Next, this plant was modified to include the first heat exchanger 140 and two holding vessels 120 were added to increase residence time (i.e., FIG. 3 configuration). FIG. 10 presents measurements of residual ionic chlorides found in samples taken from the bottom of the azeotrope column 180, comparing the FIG. 2 and FIG. 3 configurations, each over time. Residual chlorides were determined by titration using a silver nitrate solution, as described above. The data for the FIG. 2 configuration have an average of 671 ppm chloride with a standard deviation of 370 ppm chloride, whereas the data for the FIG. 3 configuration have an average of 35 ppm chloride and a standard deviation of 25 ppm chloride. The data thus show a dramatic reduction in chloride levels for the FIG. 3 configuration vs. the FIG. 2 configuration. It is predicted this reduction would be even greater for the configurations according to FIGS. 4 and 6, in which four holding vessels 120 are used to provide a residence time of four hours at 70° C. FIG. 11 presents measurements of methyl chloroformate concentration entering and exiting the fluid passageway 110 of the FIG. 3 concentration. In other words, the points signified by "+" and labeled "MCF feed to Phase 0" in FIG. 11 correspond to measurements on the mixture as it was entering the fluid passageway 110; these points have an average value of 930 parts per million by weight (ppmw) and a standard deviation of 412 ppmw. And the points signified by "■" and labeled "MCF from Phase 0" correspond to measurements on the mixture as it exits the fluid passageway 110; these points have an average value of 45 ppmw and a standard deviation of 77 ppmw. These data clearly show that an apparatus according to FIG. 3 is effective to dramatically reduce the concentration of methyl chloroformate in the process stream.

TABLE III

| Conditions | Ex. 7 (FIG. 2 Configuration) | Control Ex. 2 (FIG. 3 Configuration) |
|---|---|---|
| Mass Ratio MeOH/O$_2$/CO | 0.7/0.06/1 | 0.7/0.06/1 |
| Catalyst Content | Fixed | Fixed |
| Reaction Temperature (° C.) | 133 | 133 |
| Reaction Pressure (barg) | 23 | 23 |
| Temp. of Pre-Residence Time Heater (° C.) | 60 | — |
| Temp. of Acid Column Feed Vaporizer (° C.) | 90 | 90 |
| Residence Time between flash vessel and acid column, excluding both (hours) | 2 | 0.03 |

[t2]

TABLE IV

| Configuration | average chloride concentration ± standard deviation (ppm) |
|---|---|
| FIG. 3 (comparison) | 671 ± 370 |
| FIG. 2 (invention) | 35 ± 25 |

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

Where not specifically defined herein, technical terms in this specification may be interpreted according to Grant and Hach's Chemical Dictionary, 5$^{th}$ ed., McGraw-Hill, Inc.

All cited patents and other references are incorporated herein by reference in their entirety.

The invention claimed is:

1. A method of preparing dimethyl carbonate, comprising:
   reacting methanol, oxygen, carbon monoxide, and a catalyst to form a mixture comprising dimethyl carbonate, methyl chloroformate, hydrochloric acid, water, carbon dioxide, and carbon monoxide; and
   subjecting said mixture to conditions comprising a water concentration ($[H_2O]$), a methanol concentration ($[MeOH]$), a temperature (T), and a residence time (t), such that a parameter X calculated according to the expression $$X = exp\{-[(2.09 \times 10^9)e^{(-6381/T)}[H_2O] + (4.14 \times 10^{10})e^{(-7673/T)}[MeOH]]t\}$$

has a value less than about 0.9, wherein said water concentration and said methanol concentration are expressed in moles per milliliter, said temperature is expressed in degrees Kelvin, and said residence time is expressed in minutes.

2. The method of claim 1, wherein said parameter X has a value less than about 0.2.

3. The method of claim 1, wherein said parameter X has a value less than about 0.1.

4. The method of claim 1, wherein said parameter X has a value less than about 0.05.

5. The method of claim 1, wherein said parameter X has a value less than about 0.01.

6. The method of claim 1, wherein said water concentration is about 0.1 to about 50 moles per liter.

7. The method of claim 1, wherein said methanol concentration is about 1 to about 25 moles per liter.

8. The method of claim 1, wherein said temperature is about 30° C. to about 130° C.

9. The method of claim 1, wherein said residence time is about 0.5 hour to about 10 hours.

10. The method of claim 1, further comprising removing hydrochloric acid from said mixture.

11. The method of claim 10, wherein said removing hydrochloric acid comprises reducing the concentration of said hydrochloric acid to less than about $1 \times 10^{-3}$ moles per liter.

12. A method of preparing dimethyl carbonate, comprising:
   reacting methanol, oxygen, carbon monoxide, and a catalyst to form a mixture comprising dimethyl carbonate, methyl chloroformate, hydrochloric acid, water, carbon dioxide, and carbon monoxide;
   subjecting said mixture to conditions comprising an initial concentration of methyl chloroformate ($[MCF]_{t=0}$), a water concentration ($[H_2O]$), a methanol concentration ($[MeOH]$), a temperature (T), and a residence time (t), such that a parameter Z calculated according to the expression $$Z = [MCF]_{t=0} exp\{-[(2.09 \times 10^9)e^{(-6381/T)}[H_2O] + (4.14 \times 10^{10})e^{(-7673/T)}[MeOH]]t\}$$

has a value less than about $5 \times 10^{-6}$, wherein said initial concentration of methyl chloroformate, said water concentration, and said methanol concentration are expressed in moles per milliliter, said temperature is expressed in degrees Kelvin, and said residence time is expressed in minutes.

13. The method of claim 12, wherein said initial concentration of methyl chloroformate is about $5 \times 10^{-6}$ to about $5 \times 10^{-4}$ moles per liter.

14. The method of claim 12, further comprising removing hydrochloric acid from said mixture.

15. A method of preparing a dialkyl carbonate, comprising:
   reacting methanol, oxygen, carbon monoxide, and a catalyst to form a mixture comprising dimethyl carbonate, methyl chloroformate, hydrochloric acid, water, carbon dioxide, and carbon monoxide; and
   maintaining said mixture at a temperature of about 50° C. to about 80° C. for about 1 hour to about 10 hours.

16. The method of claim 15, further comprising removing hydrochloric acid from said mixture.

17. A method of preparing dimethyl carbonate, comprising:
   reacting methanol, oxygen, carbon monoxide, and a catalyst to form a mixture comprising dimethyl carbonate, methyl chloroformate, hydrochloric acid, water, carbon dioxide, and carbon monoxide; and
   subjecting said mixture to conditions comprising an initial dimethyl carbonate concentration ($[DMC]_{t=0}$), an initial water concentration ($[H_2O]_{t=0}$), an initial methanol concentration ($[MeOH]_{t=0}$), an initial hydrochloric acid concentration ($[HCl]_{t=0}$), a temperature (T), and a residence time (t), such that a parameter X calculated according to the expression $$X = exp\{-[(2.09 \times 10^9)e^{(-6381/T)}[H_2O]_{t=0}(4.14 \times 10^{10})e^{(-7673/T)}[MeOH]_{t=0}]t\}$$

has a value less than about 0.9, and a parameter Y calculated according to the expression $$Y = \frac{\left(1 - \frac{[H_2O]_{t=0}}{[DMC]_{t=0}}\right)}{\left(1 - \left(\frac{[H_2O]_{t=0}}{[DMC]_{t=0}}\right)\left(exp\left((6.6 \times 10^{10})(exp(-6636/T))[HCl]_{t=0}[DMC]_{t=0}\left(\frac{[H_2O]_{t=0}}{[DMC]_{t=0}} - 1\right)t\right)\right)\right)}$$

has a value of at least about 0.9, wherein said initial dimethyl carbonate concentration, said initial water concentration, said initial methanol concentration, and said initial hydrochloric acid concentration are expressed in moles per milliliter, said temperature is expressed in degrees Kelvin, and said residence time is expressed in minutes.

18. The method of claim 17, wherein said parameter Y has a value of at least about 0.95.

19. The method of claim 17, wherein said parameter Y has a value of at least about 0.99.

20. The method of claim 17, wherein said initial dimethyl carbonate concentration is about 0.5 to about 10 moles per liter.

21. The method of claim 17, wherein said initial hydrochloric acid concentration is about $1\times10^{-3}$ to about $2\times10^{-1}$ moles per liter.

22. The method of claim 17, further comprising removing hydrochloric acid from said mixture.

23. A method of preparing dimethyl carbonate, comprising:

reacting methanol, oxygen, carbon monoxide, and a catalyst to form a mixture comprising dimethyl carbonate, methyl chloroformate, hydrochloric acid, water, carbon dioxide, and carbon monoxide; and subjecting said mixture to conditions comprising a water concentration ($[H_2O]$), a methanol concentration ($[MeOH]$), a temperature (T), and a residence time (t), such that a parameter X' calculated according to the expression $$X'=1/[1+[(2.09\times10^9)e^{(-6381/T)}[H_2O]+(4.14\times10^{10})e^{(-7673/T)}[MeOH]]t]$$

has a value less than about 0.5, wherein said water concentration and said methanol concentration are expressed in moles per milliliter, said temperature is expressed in degrees Kelvin, and said residence time is expressed in minutes.

24. A polycarbonate produced by the reaction of a diaryl carbonate with a dihydric phenol wherein the diaryl carbonate is produced by the reaction of an aryl hydroxide with the dimethyl carbonate produced by the method of claim 1.

25. A polycarbonate produced by the reaction of a diaryl carbonate with a dihydric phenol wherein the diaryl carbonate is produced by the reaction of an aryl hydroxide with the dimethyl carbonate produced by the method of claim 12.

26. A polycarbonate produced by the reaction of a diaryl carbonate with a dihydric phenol wherein the diaryl carbonate is produced by the reaction of an aryl hydroxide with the dialkyl carbonate produced by the method of claim 15.

27. A polycarbonate produced by the reaction of a diaryl carbonate with a dihydric phenol wherein the diaryl carbonate is produced by the reaction of an aryl hydroxide with the dimethyl carbonate produced by the method of claim 17.

28. A polycarbonate produced by the reaction of a diaryl carbonate with a dihydric phenol wherein the diaryl carbonate is produced by the reaction of an aryl hydroxide with the dimethyl carbonate produced by the method of claim 23.

* * * * *